United States Patent [19]

Hunt et al.

[11] Patent Number: 4,540,577

[45] Date of Patent: Sep. 10, 1985

[54] DYNAMATE II MINERAL NUTRITION SUPPLEMENT

[75] Inventors: Richard B. Hunt, Vernon Hills, Ill.; William B. Dancy; James B. Alexander, both of Carlsbad, N. Mex.

[73] Assignee: International Minerals & Chemical Corp., Terre Haute, Ind.

[21] Appl. No.: 515,730

[22] Filed: Jul. 21, 1983

[51] Int. Cl.$^3$ .................... A61K 33/14; A61K 33/06; A61K 33/04; A61K 9/00

[52] U.S. Cl. .................................. 424/153; 424/154; 424/162; 424/16

[58] Field of Search ................ 424/153, 154, 162, 16; 426/2

[56] References Cited

U.S. PATENT DOCUMENTS

| | | |
|---|---|---|
| 2,927,859 | 3/1960 | Gordon ........................... 424/154 X |
| 3,342,577 | 9/1919 | Blouin et al. ........................... 424/16 |
| 3,826,827 | 7/1974 | Forest et al. ........................ 424/162 |
| 3,897,550 | 7/1975 | Reynolds ............................ 424/153 |
| 4,118,513 | 10/1978 | Braund et al. .......................... 426/2 |
| 4,376,790 | 3/1983 | Ames ....................................... 426/2 |

Primary Examiner—Frederick E. Waddell
Attorney, Agent, or Firm—Robert H. Dewey

[57] ABSTRACT

A nutritional mineral supplement for animal feeds comprising amorphous sulfur, potassium chloride and langbeinite when prepared by mixing same, heating the mixture to above 107° C., adding amorphous sulfur with agitation and allowing the mixture to cool.

3 Claims, No Drawings

DYNAMATE II MINERAL NUTRITION SUPPLEMENT

This invention relates to a mineral nutrition supplement. In a particular aspect, this invention relates to an improved nutritional supplement for supplying minerals to animal feed rations.

Langbeinite, which is a naturally occurring mineral, is the double salt of potassium and magnesium sulfates. It is used in purified form in animal feed rations as a rich source of sulfur, potassium and magnesium dietary essentials for livestock and poultry. It is especially useful in formulas where forages and oilmeals are replaced with ingredients which are low in these minerals. Langbeinite is slowly soluble, thereby supplying these elements at a controlled rate for optimum use by rumen microorganisms.

Sulfur is utilized by rumen bacteria to produce essential amino acids. High energy rations containing non-protein nitrogen sources may be inadequate in sulfur from natural sources. The sulfate radical can spare excess methionine in poultry rations, reducing costs without impairing feed performance.

Potassium is essential for maximum activity of the rumen micropopulation. It is also essential for optimum metabolism of every cell in the body. Potassium promotes optimum feed intake and performance and, therefore, should be added to rations which are borderline or deficient in this element.

Magnesium is essential to meet animals' requirements for growth, production and reproduction. Feeds formerly contained considerable amounts of forages which provided adequate levels of magnesium. However, modern high-energy rations tend to be deficient in magnesium and the rations should, therefore, be fortified.

Langbeinite is more palatable than soluble magnesium or sulfur compounds. It is readily consumed-free choice or in feed or mineral mixtures. It has been widely accepted by animal growers, but improved products are always desirable in this industry.

SUMMARY OF THE INVENTION

It is an object of this invention to provide a mineral nutrition supplement.

It is another object of this invention to provide an improved mineral nutritional supplement for animal feed rations.

Other objects of this invention will be apparent to those skilled in the art from the disclosure herein.

It is the discovery of this invention to provide an improved mineral nutritional supplement. The improved composition provides for higher potassium and higher sulfur with only slightly lower magnesium content. The improved product comprises potassium sulfate, magnesium sulfate, potassium chloride and sulfur generally in a ratio of approximately 35.5:49.0:10.0:5.5 parts by weight, respectively. The magnesium and potassium sulfates can be conveniently provided by langbeinite, 84.5 parts. It is understood that these ratios are not critical and departure from them may be made without departing from the concept of this invention.

DETAILED DISCUSSION

The potassium chloride used in the practice of this invention is of sufficient purity to be acceptable for use in animal feed rations. A preferred product is DYNA-K brand, marketed by International Minerals & Chemical Corporation. It is not less than 95.0% KCl and has a typical sieve analysis as follows:

| Mesh | % |
| --- | --- |
| +14 | 4 |
| +20 | 23 |
| +28 | 55 |
| +35 | 76 |
| +48 | 90 |
| +65 | 96 |

It is understood that the practice of this invention is not limited to DYNA-K nor to the foregoing sieve analysis.

The sulfur used in the practice of this invention is of a purity suitable for use in animal feed ration. It is amorphous, and, consequently, is in finely divided form.

Although the magnesium and potassium sulfates may be used as separate compounds, it is more convenient, and hence preferred, to add them as langbeinite. The langbeinite, when used in the practice of this invention, is of a purity suitable for use in animal feed ration. A suitable and preferred product is a coarse grade of DYNAMATE brand of double sulfate of potassium and magnesium marketed by International Minerals & Chemical Corporation. It has a guaranteed analysis of not less than 22% sulfur, 18% potassium and 11% magnesium. For the practice of this invention, the preferred sieve analysis is comparable to that of the potassium chloride so that segregation will be minimized.

The mixture of the present invention can be prepared by simply mixing the ingredients in the desired proportion, e.g. amorphous sulfur, 3-7%, preferably 5-6%; potassium chloride, 0-13%, preferably 8-12%; and langbeinite, 80-97%, preferably 82-87%.

Dusting and/or segregation of this mixture may be controlled by adding one to two gallons per ton of a nutritionally acceptable vegetable or mineral oil, many of which are known.

It is an embodiment of the present invention to provide a process for preparing the mixture. The process provides a product which is free from dusting and segregation. According to the preferred process, the potassium chloride and langbeinite are mixed in the preferred proportions and the mixture is then heated to above the melting point of sulfur, i.e. to above about 107° C. (225° F.), preferably about 110-115° C. The sulfur is then added gradually to the heated mixture with thorough agitation. The sulfur melts and coats the mixture, which is then allowed to cool. The resulting product is free from fines and dust.

In another embodiment, only the langbeinite without the potassium chloride is heated to above 107° C., then the sulfur is added with thorough agitation. The mixture is cooled to any temperature below the melting point of sulfur and the potassium chloride, if any, is blended in. This latter step can be done promptly or at any later time desired. With reference to the above-described proportions, this embodiment provides langbeinite coated with sulfur in a ratio of from 3 to 8.75 parts of sulfur per 100 parts of mixture.

The mixture of this invention, which for convenience has been designated Dynamate II brand of double sulfate of potassium and magnesium, is used in animal feed rations in the same proportions as is known for langbeinite, namely within the range of about 3-40 lb/ton (0.15-2.0%). The following table exemplifies typical proportions. In animal mineral feeds considerably higher proportions would be used, namely from about 100 to 260 lb/ton (5%–13%).

| Dairy | Dynamate II lb/ton | Beef | Dynamate II lb/ton |
|---|---|---|---|
| 16% protein | 5–20 | Feedlot | 5–20 |
| 18% protein | 10–20 | 20% Range | 10–20 |
| 20% protein | 10–20 | 32% Supplement | 20–40 |
| 24% protein | 15–25 | 40% Supplement | 20–40 |
| 36% protein | 20–30 | 45% Supplement | 30–40 |
| Swine | | | Dynamate II |
| Pig and Hog Feed | | | 5 lb/ton |
| Gestation | | | 5 lb/ton |
| Lactation | | | 5 lb/ton |
| Pig and Sow, 36% | | | 20 lb/ton |
| Hog Supplement, 40% | | | 25 lb/ton |
| Turkey, complete feeds | | | 5–10 |
| Chickens, complete feeds | | | 3–5 |

The invention will be better understood with reference to the following examples. It is understood that the examples are intended only to illustrate the invention and it is not intended that the invention be limited thereby.

EXAMPLE 1

A mixture was prepared consisting of 5.5% amorphous sulfur (a find powder), 10% of animal feed grade potassium chloride (DYNA-K brand, marketed by International Minerals & Chemical Corporation) and 84.5% langbeinite. It was observed that the mixture did not have a desirable uniform color. When "distressed", to simulate handling, a test for dust resulted in three times the acceptable dust level. The product after test had lost a significant amount of sulfur.

The foregoing experiment was repeated except that a vegetable oil mixture of soybean and corn oil was added to the mixture at a proportion of one gallon per ton of product. Dusting was minimal after "distressing" but some sulfur segregation was observed. However, the product was determined to be acceptable for the intended use.

EXAMPLE 2

Potassium chloride, 10 lb, and langbeinite, 84.5 lb, were blended and then heated to 235° F. (113° C.). Amorphous sulfur, 5.5 lb, was added gradually with thorough blending. The resulting product was free from segregation and dusting.

EXAMPLE 3

Langbeinite 87 lb is heated to 113° C. Amorphous sulfur 5 lb is added gradually with thorough blending. The mixture is permitted to cool to ambient temperature and potassium chloride 8 lb is mixed in with thorough blending. The resulting product is free from segregation and dusting.

EXAMPLE 4

Langbeinite 97 lb is heated to 113° C. Amorphous sulfur 3 lb is added gradually with thorough blending. The mixture is permitted to cool to ambient temperature. The product obtained thereby is langbeinite coated with sulfur. It is free from dusting.

EXAMPLE 5

The experiment of Example 2 is repeated in all essential details except that 82 lb of langbeinite, 12 lb of potassium chloride and 6 lb of sulfur are used.

EXAMPLE 6

The experiment of Example 2 is repeated in all essential details except that 80 lb of langbeinite, 13 lb of potassium chloride and 7 lb of sulfur are used.

We claim:

1. A nutritional mineral supplement for animal feeds comprising amorphous sulfur, potassium chloride and langbeinite prepared by the process consisting essentially of the steps of (a) forming a mixture of potassium chloride 0–13 parts and langbeinite 80–97% parts, (b) heating the mixture to above about 107° C., (c) slowly adding with agitation from about 3–7 parts of amorphous sulfur and (d) cooling the resulting mixture.

2. The mineral supplement of claim 1 comprising sulfur 5–6%, potassium chloride 0–12% and langbeinite 82–87%.

3. The mineral supplement of claim 2 wherein the sulfur is present in a concentration of about 5.5%, potassium chloride about 10% and langbeinite about 84.5%.

* * * * *